[19] United States Patent
Wolford

[11] 4,125,535
[45] Nov. 14, 1978

[54] PROCESS FOR PREPARING BISIMIDES AND BISIMIDES PREPARED THEREBY

[75] Inventor: Lionel T. Wolford, Freehold, N.J.

[73] Assignee: Cities Service Company, Tulsa, Okla.

[21] Appl. No.: 766,098

[22] Filed: Feb. 7, 1977

Related U.S. Application Data

[62] Division of Ser. No. 693,027, Jun. 4, 1976, abandoned.

[51] Int. Cl.$^2$ ............................................ C07D 209/34
[52] U.S. Cl. ................................................ 260/326 N
[58] Field of Search .................................... 260/326 N

[56] References Cited

U.S. PATENT DOCUMENTS

| | | | |
|---|---|---|---|
| 3,051,724 | 8/1962 | Bolton et al. | 260/325 |
| 3,873,567 | 3/1975 | Cyba | 260/326 C |

FOREIGN PATENT DOCUMENTS 1,951,632  10/1969  Fed. Rep. of Germany ...... 260/326 N

*Primary Examiner*—Ethel G. Love
*Attorney, Agent, or Firm*—Patricia J. Hogan

[57] ABSTRACT

White N,N'-alkylene-bis-tetrabromophthalimides are prepared by reacting about two molar proportions of tetrabromophthalic anhydride with about one molar proportion of a diaminoalkane containing 2–6 carbon atoms in a solvent mixture having a boiling point of at least about 125° C. and comprising about 50–97.5% by weight of a liquid aromatic hydrocarbon or halohydrocarbon having a boiling point of at least about 80° C. and about 50–2.5% by weight of an alkanoic or aralkanoic acid having a dissociation constant not higher than about $6 \times 10^{-5}$ at 25° C. A preferred solvent is a mixture of about 70% by weight of xylenes and about 30% by weight of propionic acid having a boiling point of about 130° C. The products are particularly useful as flame retardants.

12 Claims, No Drawings

PROCESS FOR PREPARING BISIMIDES AND BISIMIDES PREPARED THEREBY

This is a division, of application Ser. No. 693,027, filed June 4, 1976, now abandoned.

BACKGROUND OF THE INVENTION

1. Field of the Invention

This invention relates to bisimides and more particularly relates to white N,N'-alkylene-bis-tetrabromophthalimides and to a process for preparing them.

2. Description of the Prior Art

As described in U.S. Pat. Nos. 3,624,024 (Caldwell et al.) and 3,873,567 (Cyba), British Pat. No. 1,287,934 (Raychem), and Sydney M. Spatz and Herman Stone, "Some N-Substituted Tetrabromophthalimide Fire-Retardant Additives," INDUSTRIAL AND ENGINEERING CHEMISTRY PRODUCT RESEARCH AND DEVELOPMENT, Volume 8, pp. 397-398 (1969), it is known that N,N'-alkylene-bis-tetrabromophthalimides can be prepared and that they are useful as flame retardants for many normally flammable materials. However, as indicated by Raychem's Example 16, and as can be determined by repeating Cyba's Example VII, prior art processes for preparing these bisimides have resulted in poor yields and colored products when diaminoalkanes other than hexamethylenediamine have been used as reactants. The poor yields have made these processes economically unattractive, and the coloration of the products has prevented their use as flame retardants in many applications.

SUMMARY OF THE INVENTION

An object of this invention is to provide white N,N'-alkylene-bis-tetrabromophthalimides wherein the alkylene group contains 2-6 carbon atoms.

Another object is to provide a novel process for preparing such bisimides in good yields.

These and other objects are attained by reacting about two molar proportions of tetrabromophthalic anhydride with about one molar proportion of a diaminoalkane containing 2-6 carbon atoms in a solvent mixture having a boiling point of at least about 125° C. and comprising about 50-97.5% by weight of a liquid aromatic hydrocarbon or halohydrocarbon having a boiling point of at least about 80° C. and about 50-2.5% by weight of an alkanoic or aralkanoic acid having a dissociation constant not higher than about $6 \times 10^{-5}$ at 25° C.

DESCRIPTION OF THE PREFERRED EMBODIMENTS

The diaminoalkane that is reacted with tetrabromophthalic anhydride in the practice of the invention may be any diaminoalkane containing 2-6 carbon atoms, e.g., 1,2-diaminoethane, 1,2-diaminopropane, 1,3-diaminopropane, 1,4-diaminobutane, 1,5-diaminopentane, 1,6-diaminohexane, etc. However, since a white product can be prepared by conventional techniques when the diaminoalkane is 1,6-diaminohexane, the invention is particularly useful for the preparation of bisimides from the lower diaminoalkanes containing 2-5 carbon atoms; and it is especially valuable for the preparation of a bisimide from 1,2-diaminoethane.

The liquid aromatic hydrocarbon or halohydrocarbon of the solvent mixture may be any such compound having a boiling point of at least about 80° C., e.g., benzene, toluene, xylene, mesitylene, pseudocumene, chlorobenzene, dichlorobenzene, etc., and mixtures thereof. However, it is preferably one or more isomers of xylene. This component constitutes about 50-97.5%, preferably about 60-80%, and most preferably about 65-75%, by weight of the solvent mixture.

The acid of the solvent mixture may be any alkanoic or aralkanoic acid having a dissociation constant not higher than about $6 \times 10^{-5}$ at 25° C., e.g., phenylacetic, p-methylphenylacetic, alpha-phenylpropionic, beta-phenylpropionic, diethylacetic, acetic, gammaphenylbutyric, isovaleric, valeric, isocaproic, isobutyric, butyric, propionic, hexanoic heptanoic, octanoic, and trimethylacetic acids, etc., and mixtures thereof. However, it is preferably an alkanoic acid containing 2-6 carbon atoms, most preferably propionic acid. This component constitutes about 2.5-50% by weight of the solvent mixture. However, since the products of the process, although still white, approach yellow in color when the lower concentrations of acid are employed, and viscosity may become a problem when the higher concentrations of acid are used, it is usually preferred that the acid comprise about 20-40%, most preferably about 25-35%, by weight of the solvent mixture.

Desirably the solvent mixture is composed of such aromatic (halo)hydrocarbon and acid components as are described above that are combinable in suitable proportions to produce a mixture having a boiling point of at least about 125° C. Actually, a solvent mixture having a lower boiling point would not prevent the attainment of the objects of the invention, but the reaction would be too slow to be practical if lower boiling mixtures were used. The boiling point of the mixture may be as high as is desired, but is is usually preferred to use a solvent mixture having a boiling point not higher than about 250° C. to facilitate removal of the solvent from the product. According to a preferred embodiment of the invention, the solvent mixture is a mixture of about 70% by weight of mixed xylenes and about 30% by weight of propionic acid and has a boiling point of about 130° C. The amount of solvent employed is not critical but is usually such as to provide a solids content of about 10-25% by weight.

Except for the aspects mentioned above, i.e., the use of a particular type of solvent mixture and the use of a particular ratio of reactants, the manner of reacting the tetrabromophthalic anhydride with the diaminoalkane is not critical. The reaction can be conducted by conventional condensation reaction techniques. However, it is advantageous to conduct the reaction by (1) dispersing the tetrabromophthalic anhydride in the solvent mixture, (2) heating the dispersion to about 90°-115° C., (3) then adding the diaminoalkane gradually, e.g., over a period of about 0.5-3 hours, and (4) refluxing the reaction mixture while removing water of reaction, e.g., in a DeanStark trap, until the water of reaction is completely removed. The product may then be recovered by conventional cooling, filtering, washing, and drying techniques.

The process of the invention is advantageous in that it provides a technique of preparing novel white N,N'-alkylene-bis-tetrabromophthalimides wherein the alkylene group contains 2-5 carbon atoms, as well as an alternative method of preparing white N,N'-hexamethylene-bis-tetrabromophthalimide. The products, like the N,N'-alkylene-bis-tetrabromophthalimides of the prior art, are particularly useful as flame retardants and have the advantage of being utilizable in compositions wherein it is necessary or desirable to avoid discoloration by a flame retardant.

The following examples are given to illustrate the invention and are not intended as a limitation thereof.

EXAMPLE I

Charge 2226 g. of xylene, 954 g. of propionic acid, and 992.3 g. (2.14 moles) of tetrabromophthalic anhydride to a suitable reaction vessel. Heat the mixture to 95° C., and add 1.07 moles of 1,2-diaminoethane over a period of 0.5 hour. Then heat the reaction mixture at reflux (130°–133° C.) for about six hours while removing water of reaction. Cool the reaction mixture to 25° C., filter to separate the solid product, wash the product with one liter of methanol, and dry the product at 150° C. The process results in a 97% yield of white N,N'-ethylene-bis-tetrabromophthalimide having a melting point of 456°–471° C. d., a bromine content of 66.0%, and an acid number of 2.2.

EXAMPLE II - CONTROL

Repeat Example I except for replacing the propionic acid with the same amount of xylene. The process results in a 77% yield of a yellow product having a melting point greater than 405° C., a bromine content of 62.5%, and an acid number of 9.6.

EXAMPLE III

Repeat Example I except for replacing the 1,2-diaminoethane with 1,3-diaminopropane. The process results in a 90% yield of white N,N'-(1,3-propylene)-bis-tetrabromophthalimide having a melting point of 334°–334° C. d., a bromine content of 64.0%, and an acid number of 2.1.

EXAMPLE IV - CONTROL

Repeat Example III except for replacing the propionic acid with the same amount of xylene. The process results in a 54% yield of a yellow-orange product having a melting point of 315°−>400° C, d., a bromine content of 61.0%, and an acid number of 5.0.

EXAMPLE V

Repeat Example I except for replacing the 1,2-diaminoethane with 1,2-diaminopropane. The process results in a 97% yield of white N,N'-(1,2-propylene)-bis-tetrabromophthalimide having a melting point greater than 500° C., a bromine content of 64.1%, and an acid number of 0.6.

EXAMPLE VI

Repeat Example I except for replacing the 1,2-diaminoethane with 1,6-diaminohexane. The process results in a 98% yield of white N,N'-hexamethylene-bis-tetrabromophthalimide having a melting point of 364°–368° C. d., a bromine content of 62.3%, and an acid number of 0.1.

Similar results are observed when the 1,2-diaminoethane is replaced by 1,4-diaminobutane or 1,5-diaminopentane.

It is obvious that many variations may be made in the products and processes set forth above without departing from the spirit and scope of this invention.

What is claimed is:

1. A process for preparing an N,N'-alkylene-bis-tetrabromophthalimide which comprises reacting about two molar proportions of tetrabromophthalic anhydride with about one molar proportion of a diaminoalkane containing 2–6 carbon atoms in a solvent mixture having a boiling point of at least about 125° C. and comprising about 50–97.5% by weight of a liquid aromatic hydrocarbon or halohydrocarbon having a boiling point of at least about 80° C. and about 50–2.5% by weight of an alkanoic or aralkanoic acid having a dissociation constant not higher than about $6 \times 10^{-5}$ at 25° C.

2. The process of claim 1 wherein the diaminoalkane is 1,2-diaminoethane.

3. The process of claim 1 wherein the diaminoalkane is 1,2-diaminopropane.

4. The process of claim 1 wherein the diaminoakane is 1,3-diaminopropane.

5. The process of claim 1 wherein the diaminoalkane is 1,6-diaminohexane.

6. The process of claim 1 wherein the liquid aromatic hydrocarbon or halohydrocarbon is a compound selected from the group consisting of benzene, toluene, xylene, mesitylene, pseudocumene, chlorobenzene, dichlorobenzene, and mixtures thereof.

7. The process of claim 1 wherein the acid is an alkanoic acid containing 2–6 carbon atoms.

8. The process of claim 1 wherein the acid comprises about 20–40% by weight of the solvent mixture.

9. The process of claim 1 wherein the acid comprises about 25–35% by weight of the solvent mixture.

10. The process of claim 1 wherein the solvent mixture is a mixture of about 70% by weight of xylenes and about 30% by weight of propionic acid and has a boiling point of about 130° C.

11. A process for preparing an N,N'-alkylene-bis-tetrabromophthalimide which comprises (1) dispersing about two molar proportions of tetrabromophthalic anhydride in a solvent mixture having a boiling point of at least about 125° C. and comprising about 65–75% by weight of a liquid aromatic hydrocarbon or halohydrocarbon having a boiling point of at least about 80° C. and about 35–25% by weight of an alkanoic or aralkanoic acid having a dissociation constant not higher than about $6 \times 10^{-5}$ at 25° C., (2) heating the dispersion to a temperature of about 90°–115° C., (3) gradually adding about one molar proportion of a diaminoalkane containing 2–6 carbon atoms, and (4) refluxing the reaction mixture while removing water of reaction until the water of reaction is completely removed.

12. The process of claim 11 wherein the solvent mixture is a mixture of about 70% by weight of xylenes and about 30% by weight of propionic acid and has a boiling point of about 130° C.

* * * * *